US011638719B2

(12) United States Patent
Sahin et al.

(10) Patent No.: US 11,638,719 B2
(45) Date of Patent: May 2, 2023

(54) PRODUCT FOR OBESITY TREATMENT

(71) Applicant: YEDITEPE UNIVERSITESI, Istanbul (TR)

(72) Inventors: Fikrettin Sahin, Istanbul (TR); Nezaket Turkel Sesli, Istanbul (TR); Aysu Yilmaz, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 341 days.

(21) Appl. No.: 16/492,197

(22) PCT Filed: Mar. 7, 2018

(86) PCT No.: PCT/TR2018/050082
§ 371 (c)(1),
(2) Date: Sep. 9, 2019

(87) PCT Pub. No.: WO2019/027390
PCT Pub. Date: Feb. 7, 2019

(65) Prior Publication Data
US 2020/0038434 A1 Feb. 6, 2020

(30) Foreign Application Priority Data
Mar. 9, 2017 (TR) .................. 2017/03622

(51) Int. Cl.
*A61P 3/04* (2006.01)
*A61K 47/24* (2006.01)
*A61K 31/765* (2006.01)

(52) U.S. Cl.
CPC ............ *A61K 31/765* (2013.01); *A61K 47/24* (2013.01); *A61P 3/04* (2018.01)

(58) Field of Classification Search
CPC .......... A61K 31/765; A61K 47/24; A61P 3/04
See application file for complete search history.

(56) References Cited

U.S. PATENT DOCUMENTS

| 2004/0185028 A1* | 9/2004 | Hu ........................ A01N 33/12 424/78.27 |
| 2006/0128663 A1 | 6/2006 | Holmes-Farley et al. |
| 2016/0324932 A1* | 11/2016 | Baldwin ................... A61P 5/50 |

FOREIGN PATENT DOCUMENTS

| TR | 2013/11917 | | 7/2016 |
| WO | WO20131472569 | * | 9/2013 |
| WO | WO2015/053726 | * | 4/2015 |
| WO | WO 2015053726 | * | 4/2015 |

OTHER PUBLICATIONS

Johnston et al. JPP, 2006, 58: 1099-1105. (Year: 2006).*
Aysu Yilmaz. Effect of Boron and F68 Pluronic Block Copolymer Combination on Adipogenic Differntiation of Human Adipose Stem Cells. Submitted to the Graduate School of Natural and Applied Sciences in partial fulfillment of the requirements for the degree of Master of Philosophy in Biotechnology. Sep. 12, 2014.

* cited by examiner

*Primary Examiner* — Genevieve S Alley
(74) *Attorney, Agent, or Firm* — Bayramoglu Law Offices LLC

(57) ABSTRACT

A product containing a boron compound for use in obesity treatment. By means of the present invention, a product can be obtained for obesity treatment which is not toxic to the other tissues and organs of the body. In obtaining the said product, sodium pentaborate pentahydrate, which is a poloxamer derivative, are used.

4 Claims, 7 Drawing Sheets

Specification includes a Sequence Listing.

|  | Adiponectin | FABP4 | PPARγ |
|---|---|---|---|
| F68 | | | |
| NaB | | | |
| F68 + NaB | | | |
| PC | | | |
| NC | | | |

FIG. 5

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 1
ttgccatcaa tgaccccttc a                                              21

<210> SEQ ID NO 2
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 2
cgccccactt gattttgga                                                 19

<210> SEQ ID NO 3
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 3
tatccccaac atgcccattc g                                              21

<210> SEQ ID NO 4
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 4
tggtaggcaa agtagtacag cc                                             22

<210> SEQ ID NO 5
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 5
cctattgacc cagaaagcga tt                                             22

<210> SEQ ID NO 6
<211> LENGTH: 21
<212> TYPE: DNA
<213> ORGANISM: Artificial Sequence
<220> FEATURE:
<223> OTHER INFORMATION: The sequence is synthetized.
```

```
<400> SEQUENCE: 6
cattacggag agatccacgg a                                              21

<210> SEQ ID NO 7
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 7
aaccttagat gggggtgtcc t                                              21

<210> SEQ ID NO 8
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 8
tcgtggaagt gacgcctttc                                                20
```

PRODUCT FOR OBESITY TREATMENT

CROSS REFERENCE TO THE RELATED APPLICATIONS

This application is the national phase entry of International Application No. PCT/TR2018/050082, filed on Mar. 7, 2018, which is based upon and claims priority to Turkish Patent Application No. 2017/03622, filed on Mar. 9, 2017, the entire contents of which are incorporated herein by reference.

TECHNICAL FIELD

The present invention relates to a product containing a boron compound and a Pluronic® for use in obesity treatment.

BACKGROUND

Obesity is a metabolic disease which poses a public health concern and systemic problems throughout the world [1]. Obesity is identified in individuals with a body mass index (BMI) above 30. This bears the risk of many diseases such as cardiovascular diseases (especially when the abdominal fat rate is high), diabetes, certain cancer types, psychological disorders and reproductive problems [2-6]. Obesity is diagnosed according to the BMI ratio, and changes in life standards such as diet and physical activity can be a treatment method for some patients [7]. However, in the rest of the patient profile, drugs and operational interventions are inevitable. The risks posed by the bariatric surgery (obesity surgery) makes administering an alternative effective drug treatment more attractive. It is difficult and very challenging to find remarkable new drugs for prevention and treatment of obesity. The goal of the anti-obesity drugs used clinically is generally to reduce the fat ratio in pre-adipocytes and also to break down previously stored fats [8-10]. In order to achieve this goal, mechanisms, which accelerate the metabolism or reduce hunger, while at the same time reducing the intake or absorption of fat in the foods, are used. Despite all these efforts, weight loss and weight control drugs produced by the food and health industries today are unsuccessful in long-term maintenance of weight control.

Obesity occurs due to the increase in the number of mature fat cells and the amount of fat they store as a result of the differentiation of the pre-adipocytes [11-13]. Hence, drugs that can control adipogenesis can also be useful in obesity treatment. Therefore, it is extremely important to develop a new, safe and effective drug complex to prevent adipogenesis.

Although the role and mechanism of boron for human and mammalian systems are not completely known yet, boron is an essential element for the plants and perform a function in many physiological and biochemical mechanisms [14]. Boron enters the cell specifically via the sodium-borate cotransporter (NABCI) [15, 16]. After administering a high dose of boron, metabolic disorders such as weight loss, cardiovascular problems and testicular atrophy, and toxic effects were observed in the animals [17]. In addition, it was determined that boron plays an important role in embryogenesis, bone growth and immune function in mice and it is essential for optimal health [18, 19]. It was also found that boron-deprived diet affects bone and dental development adversely [20]. Studies in rats have shown a significant decrease in bone density as a result of the boron deprivation experiments [21, 22]. In short, boron deficiency has an impact on bone growth and development. Furthermore, it has been proven that, when used in boric acid form, boron reduces periodontal inflammation and alveolar bone loss [23]. It has been proven that Boron has cytotoxic effects on various types of cancer through many different studies [24-26]. In the light of all of these studies, it can be said that dosage of boron is a critical element for animal health as well.

Although the effects of boron compounds on the lipid metabolism have not been fully elucidated at the molecular level, some animal studies have shown that oral intake of boron reduces body weight [27-29]. It has been suggested that this effect of boron is due to an increase in thermogenesis and lypogenesis occurring depending on the uncoupling protein (UCP) pathway [28] or hormonal changes.

Polymer-based technology is one of the most attractive approaches for drug research and applications. The effects of Pluronic® triblock copolymers, which can be used in many different applications on cell metabolism, also vary. When used for drug delivery purposes, Pluronic® triblock copolymers are inert and protect the drug against degradation [30]. The interaction between the plasma membrane and the Pluronics® causes inhibition of Pgp (P-glycoprotein) or MRP (Drug-resistant protein) ATPase activity [31].

Pluronic® F68, also known under the trade name Pluronic® PE6800, is a non-ionic copolymer consisting of a central polypropylene oxide and two polyethylene oxide groups [30]. Pluronic® F68 has 8350 Dalton molecular mass and is water soluble. Pluronic® F68 does not form mycelium, however it binds to the membrane surface by producing a two- or three-layer block polymer and prevents aggregation [30].

In the prior art studies, boron is used in the form of boric acid and no auxiliary agent has been used to modify the dosage and cellular ingestion. Furthermore, possible toxic effect of the high dose, which may be used to obtain sufficient effect, on the human being is another disadvantage thereof.

In the art, Pluronic® F68 has been mainly used to protect cells from destructive effects (shaking and rotation cultures) that occur during cell culturing.

The United States patent document no. US2006128663 discloses polymers comprising one or more phenyl boronate ester(s), boronamide or boronate thioester groups. The said boron containing compounds are administered in obesity treatment.

Turkish patent document no. TR20144000365 discloses an anti-obesity product containing boric acid and sodium pentaborate.

SUMMARY

An objective of the present invention is to provide a product that can be used actively in obesity treatment.

Another objective of the present invention is to provide a product for obesity treatment which is not toxic to the other tissues and organs of the body.

BRIEF DESCRIPTION OF THE DRAWINGS

"A product for obesity treatment" developed to fulfill the objectives of the present invention is illustrated in the accompanying figures wherein

FIG. 5 shows the immunocytochemistry results for Adiponectin, FABP4 and PPAR-γ proteins PC: Positive control, NC: Negative control.

DETAILED DESCRIPTION OF THE EMBODIMENTS

Figure 1:
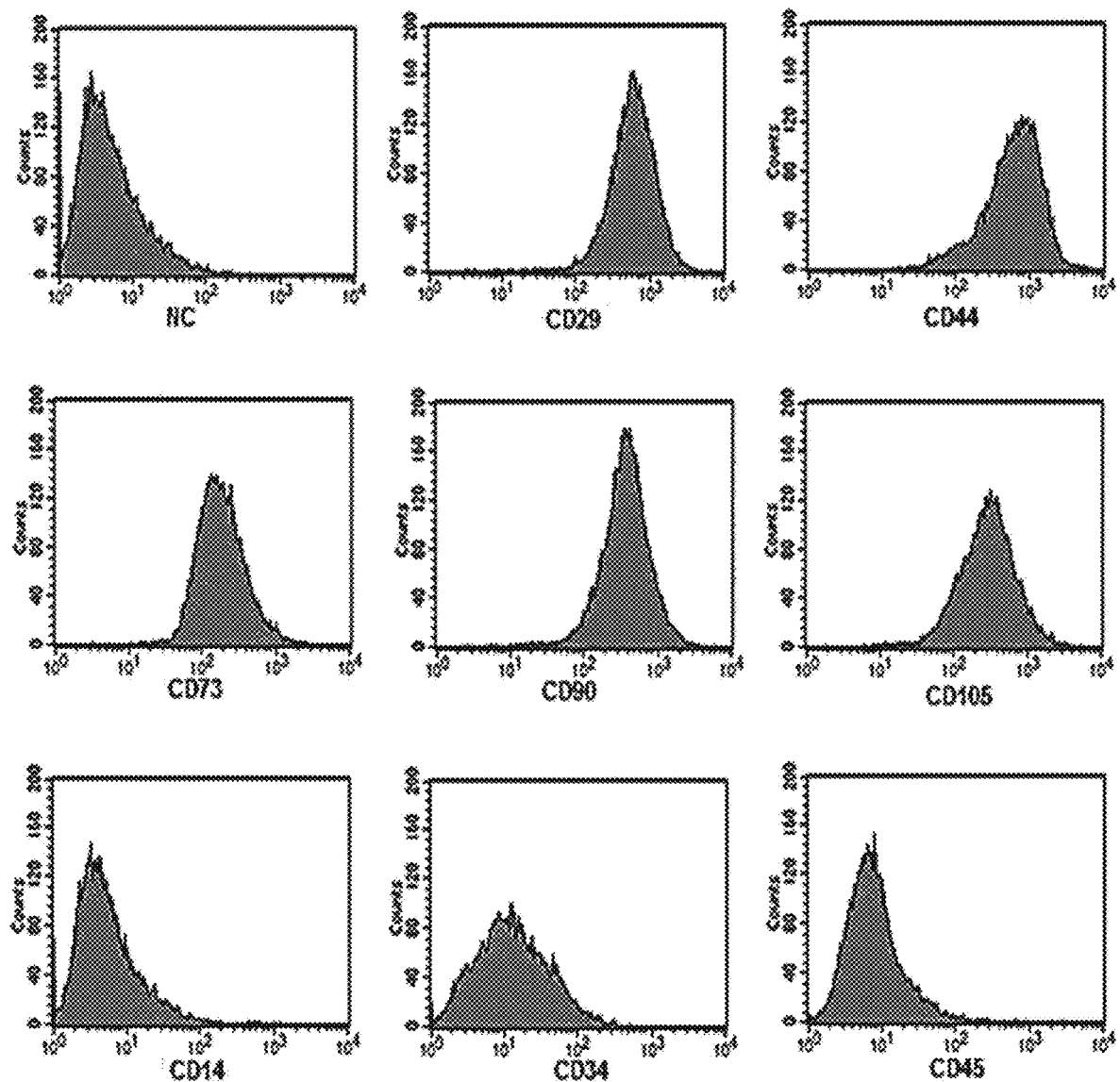
FIG. 1 is a view of the human adipose stem cell (hASCs) characterization. While hASCs were identified positive for mesenchymal stem cell surface markers (CD29, CD44, CD73, CD90, CD105), they were identified negative for hematopoietic stem cell markers (CD14, CD34, and CD45).

A boron compound and a Pluronic® poloxamer are essentially used for obtaining the product. In particular, preferably sodium pentaborate pentahydrate (NaB) was used as the boron component, and preferably Pluronic® F68 was used as the Pluronic®. The effect of the product of the present invention, which was obtained separately and in combination with these two substances, on fat differentiation was investigated. In this study, laboratory studies were carried out using human adipose stem cells (HASC).

Experimental Study

Preparation of Pluronic® F68 and Boron

Pluronic® block copolymer F68 was supplied from BASF Corporation. F68 (BASF, USA, cat. #52389638). According to the protocol described in Exner et al, 2005; F68 put in PBS on ice was dissolved with 10% (weight/volume) vortex and then filtered through a 0.2 micron filter and held at 4° C. until use [32]. In this study, F68 copolymer was tested at 1%, 0.7%, 0.5%, 0.3%, 0.1%, 0.05%, 0.01% (weight/volume).

NaB (Sodium Borate) was supplied from National Boron Research Institute BOREN (Ankara-TURKEY) and was prepared by being dissolved in DMEM medium containing 10% fetal bovine serum and 1% PSA. The stock solution of NaB dissolved at 10 mg/mL was filtered through a 0.2 micron filter and then diluted to 1 mg/ml. In this study, NaB was tested at doses of 5, 10, 20, 50, 100, 200 and 300 μg/ml.

Isolation of Human Adipose Stem Cells (HASC)

The primary human stem cells used in this study were isolated from the abdomen and upper inner thigh subcutaneous adipose tissues of two healthy female donors aged 26 and 59 years. Ethical approval of this study (decision no. 2013-529) was given by "Acibadem University Ethics Committee" and the patients were informed and their consent was taken. The adipose tissue and collagenase solution were mixed at a ratio of 1:1 and allowed to digest for 1 hour at 37° C. with shaking at 170 rpm. Then the erythrocyte lysis buffer was applied to the digested tissue and centrifuged at 2500 rpm for 7 minutes at room temperature. The pellet was re-suspended in erythrocyte lysis buffer. The cell suspension was incubated for 10 minutes at 37° C. in erythrocyte lysis buffer with continuous shaking at 170 rpm and then centrifuged at 1400 rpm for 7 minutes at room temperature. The pellet (1× without Ca/Mg) was washed with PBS and then centrifuged at 1400 rpm for 7 minutes at room temperature. The cell pellet was re-suspended in Dulbecco's Modified Eagle's Medium (DMEM) (supplemented with 10% fetal bovine serum (FBS), 1% PSA-10,000 units/ml potassium penicillin, 10,000 μg/ml streptomycin sulfate, 25 μg/ml amphotericin B-). Finally, the cells were passed through a 100 μm cell strainer and seeded in T150 plates. The cells were maintained at 37° C. and 5% $CO_2$ and were used in experiments at passages 1-5.

Characterization of HASC

The cells were trypsinized and then incubated with primary antibodies. For characterization, primary antibodies were used against CD29 (Cat #BD556049), CD34 (Cat #SC-51540), CD45 (Cat #SC-70686), CD90 (Cat #SC-53456), CD105 (Cat #SC-71043), CD14 (Cat #SC-9150), (Santa Cruz Biotechnology Inc., SantaCruz, Calif., USA) and CD73 (Cat #BD550256) (Zymed, S. San Francisco, Calif., USA). The cells were then washed with PBS to remove excess primary antibodies and incubated with fluorescein-isothiocyanate (FITC) secondary antibody (cat. no SC-2989) at 4° C. for 1 hour. For CD29, the conjugated phycoerythrin (PE)-red light-harvesting protein chromophore-conjugated monoclonal antibody was used. The flow cytometry analysis of the cells was carried out by using Becton Dickinson FACS Calibur flow cytometry system. (Becton Dickinson, San Jose, Calif., USA). 20,000 cells were counted for each sample.

Cytotoxicity Analysis for F68 Pluronic® and NaB

Cytotoxicity of Pluronic® F68 and NaB were dissolved and tested at 7 different concentrations in DMEM (W %, 0.7%, 0.5%, 0.3%, 0.1%, 0.05%, 0.01% (w/v) for F68 and 5, 10, 20, 50, 100, 200 and 300 ug/ml for NaB).

HASCs were seeded into 96-well culture plates (Corning Plasticware, Corning, N.Y., cat. no. CLS3360) at 5,000 cells/well. The next day, the cells were treated with F68 and NaB solutions that were prepared at different concentrations. In accordance with the manufacturer's instructions, cell viability was measured by the MTS assay (Promega, Southampton, UK CellTiter 96 AqueousOne solution). After 24, 48 and 72 hours of incubation, 10 ul of MTS reagent and 100 ul of DMEM medium were applied to the cells and then, after incubation at 37° C. for 2 hours, their absorbances at 409 nm were measured with the ELISA plate reader (BioTek Instruments, Inc., Vt., USA).

Adipocyte Differentiation

The cells were seeded into 6-well culture plates at 100, 000 cells/well in an adipogenic differentiation medium. Content of the medium was as follows. 10% (v/v) FBS, 1 uM dexamethasone, 100 uM indomethacin (Sigma, USA), 500 uM IBMX (Calbiochem Merck Millipore, Germany) and 0.01 mg/mL insulin (Gibco, UK). 5 different groups were prepared; only F68, only NaB, F68 and NaB combination, PC and NC. Adipogenic differentiation was applied for 10 days by changing the medium every other day. While only DMEM, 10% (v/v) FBS and 1% (v/v) PSA were applied to the negative control group, the positive control group was cultured with adipogenic differentiation medium.

Immunocytochemical Analysis—

Human adipose stem cells were seeded into 48-well plates at 8,000 cells/well. Following the differentiation experiment, the cells were fixed in 2% (w/v) paraformaldehyde at 4° C. for 30 minutes and then blocked with 2% (v/v) goat serum (Sigma, USA) for 20 minutes. The cells incubated at 4° C. overnight with PPAR-γ (ab8934, Abcam, UK, 1: 100), FABP4 (SC-30088, Santa Cruz Biotechnology, Tex., USA, 1:100) and adiponectin (ab22554, Abcam, UK, 1:50) primary antibodies were then incubated with secondary antibodies (goat anti-rabbit IgG Alexa Fluor 488, goat anti-mouse IgGAlexaFluor 488, 1:1000) at 4° C. for 2 hours. DAPI (AppliChem, Germany) was used for staining the cell nuclei, and the cells were incubated for 5 minutes at room temperature. Immunocytochemical analysis results were observed under fluorescence microscope (NiconEclipse TE200).

Real Time Polymerase Chain Reaction (RT-PCR) Analysis

Following differentiation, RNA isolation was carried out using High Pure RNA Isolation Kit (Roche, Germany) in accordance with the manufacturer's instructions. After performance of cDNA synthesis (High Fidelity cDNA synthesis kit, Roche, Germany) from isolated RNA samples, RT-PCR was performed in three replicates using iCycler RT-PCR detection system (Bio-Rad, Hercules, Calif.). Synthesis levels were normalized to GAPDH.

The following primers were used in this study:

```
GAPDH,
forward          TTGCCATCAATGACCCCTTCA,
as shown in SEQ ID NO: 1;

reverse          CGCCCCACTTGATTTTGGA,
as shown in SEQ ID NO: 2.

Adiponectin,
forward          TATCCCCAACATGCCCATTCG,
as shown in SEQ ID NO: 3;

reverse          TGGTAGGCAAAGTAGTACAGCC,
as shown in SEQ ID NO: 4.

PPARγ,
forward          CCTATTGACCCAGAAAGCGATT,
as shown in SEQ ID NO: 5;

reverse          CATTACGGAGAGATCCACGGA,
as shown in SEQ ID NO: 6.

FABP4,
forward          AACCTTAGATGGGGGTGTCCT,
as shown in SEQ ID NO: 7;

reverse          TCGTGGAAGTGACGCCTTTC,
as shown in SEQ ID NO: 8.
```

For each sample the fold changes in the expression levels were determined using the method 2 (-Delta Delta C (t)).

'Oil Red O' Staining

The 'Oil Red O' solution was prepared by dissolving 0.5 grams of 'Oil Red O' (Sigma, USA) in 100 ml of isopropanol. After being fixed with 2% paraformaldehyde (weight/volume) for 30 minutes, the cells were incubated in 'Oil Red O' solution (diluted in PBS at 6:4) for 1 hour. The cells were observed under light microscope.

Statistical Analysis

Statistical analysis of the results was performed with the unpaired t-test and the graphs were drawn using GraphPad Prism 5 software Statistical significance was accepted as $p<0.05$. In addition, a graphical representation of the results obtained from immunocytochemistry and 'Oil red O' staining was obtained using the Adobe Creative Suite 6 program Experimental Results First of all, the stem cell characterization studies were carried out before testing the effects of the boron compound and Pluronic® copolymer combination, which inhibits the differentiation of human adipose stem cells (hASCs) thereby reducing fat storage capacity, on cell viability. As noted in the literature, positive cells were selected by the mesenchymal stem cell markers and negative cells were selected by the hematopoietic stem cell markers (FIG. 1).

Figure 2:
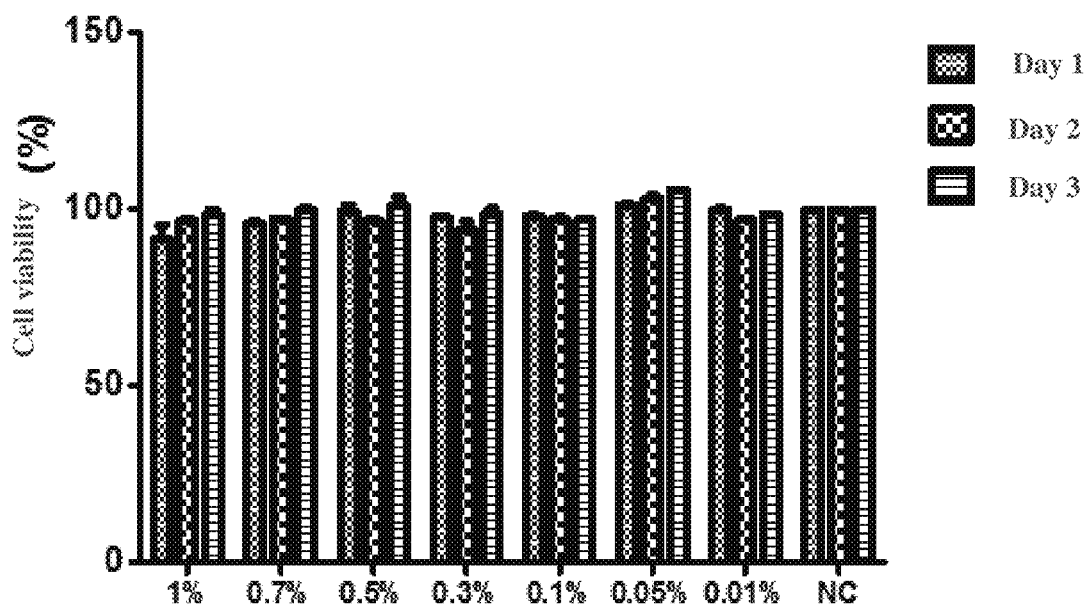
FIG. 2 is the effect of F68 copolymer on cell viability at different concentrations. NC: Negative control.

The effect of the F68 copolymer on cell viability was tested for 3 days and a ratio of 0.05% (101%, 103% and 105%, respectively at the end of day 1, day 2 and day 3), which was not toxic and which increased cell viability within this period, was selected for further experiments (FIG. 2).

Figure 3:
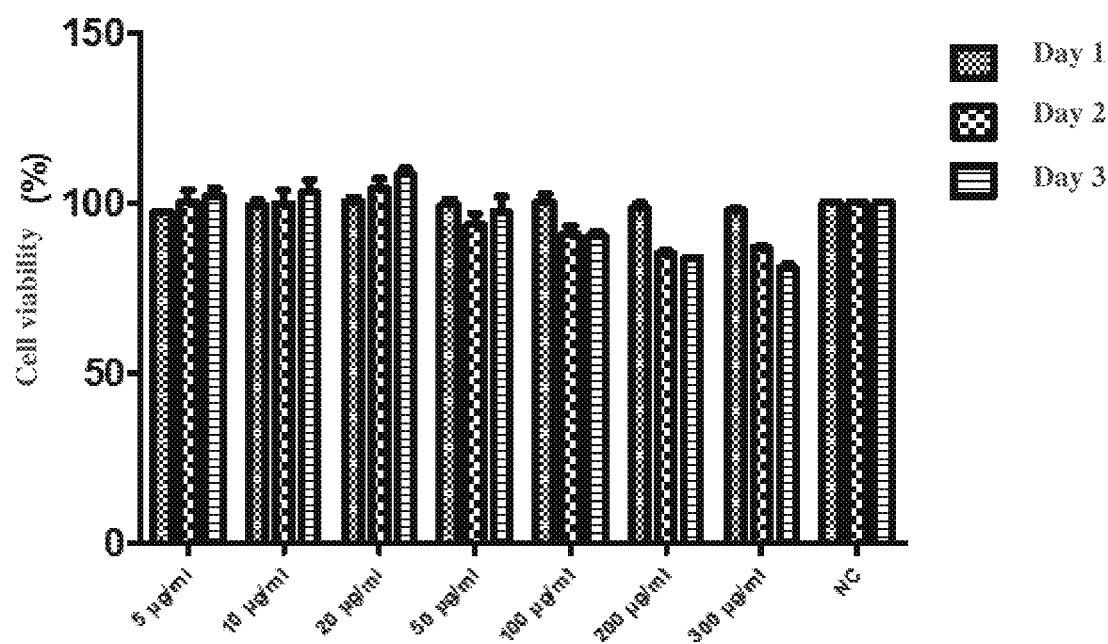
FIG. 3 is the effect of NaB on cell viability at different concentrations. NC: Negative control.

20 µg/ml dosage of the sodium pentaborate pentahydrate (NaB) boron compound: which increased cell viability of hASCs by 101% at the end of day 1, 106% at the end of day 2, and 109% at the end of day 3; was selected for the ongoing experiments (FIG. 3).

Figure 4:
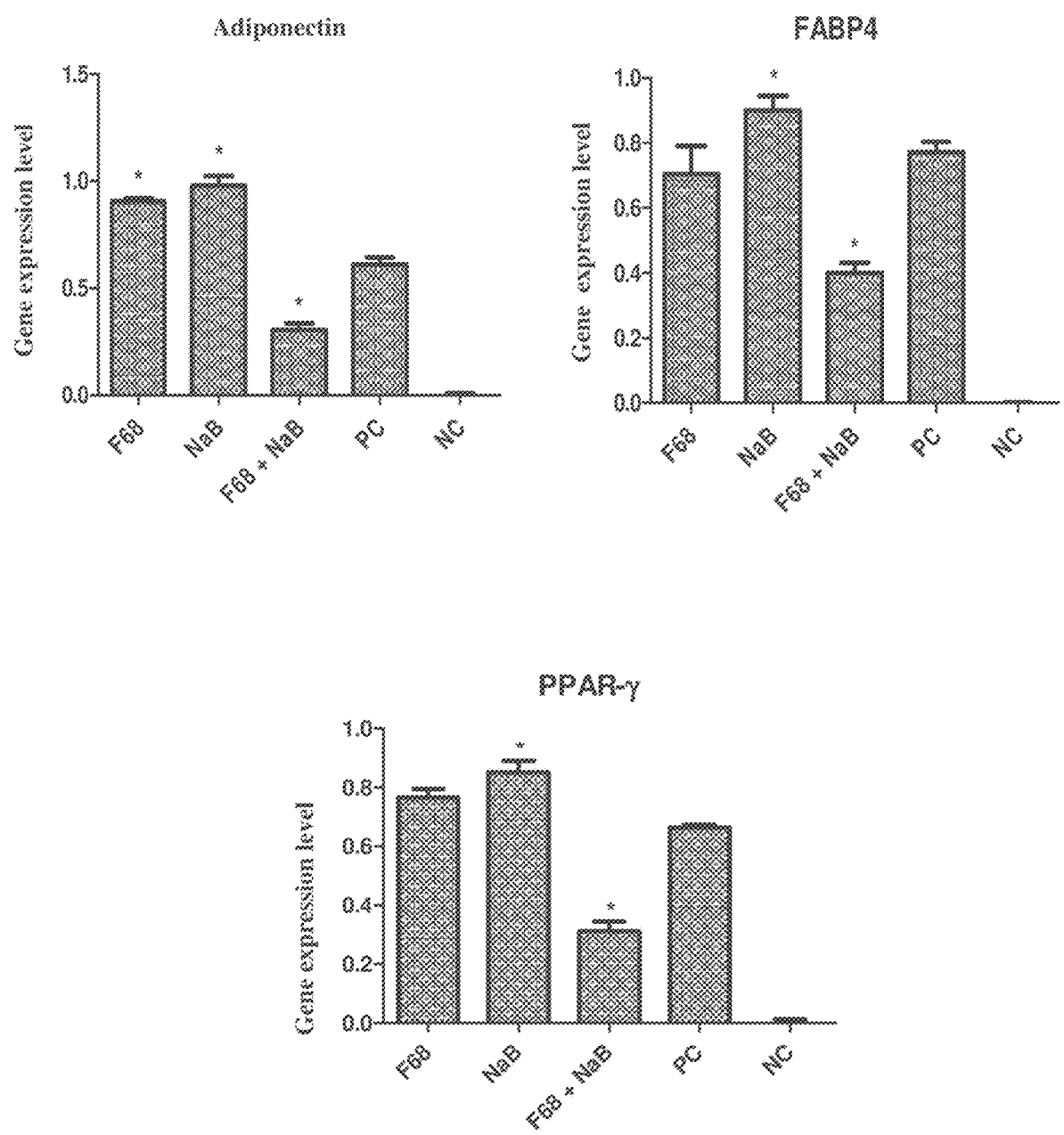
FIG. 4 shows PPAR-γ, FABP4 and Adiponectin gene expression levels in NaB, F68, both combined and control groups. NaB: Sodium pentaborate pentahydrate, PC: Positive control, NC: Negative control. *$p<0.05$ compared to positive control.

Expression levels of adipogenesis-promoting genes such as Peroxisome proliferator-activated receptor-γ (PPARγ), fatty acid binding protein (FABP4) and adiponectin were analyzed by real-time polymerase chain reaction. When the specified dosages of F68 copolymer and NaB were administered alone, the expression levels of these three genes increased significantly compared to the positive control. However, it was shown that gene expression with the combination of F68 and NaB was significantly suppressed relative to positive control (FIG. 4).

Figure 5:
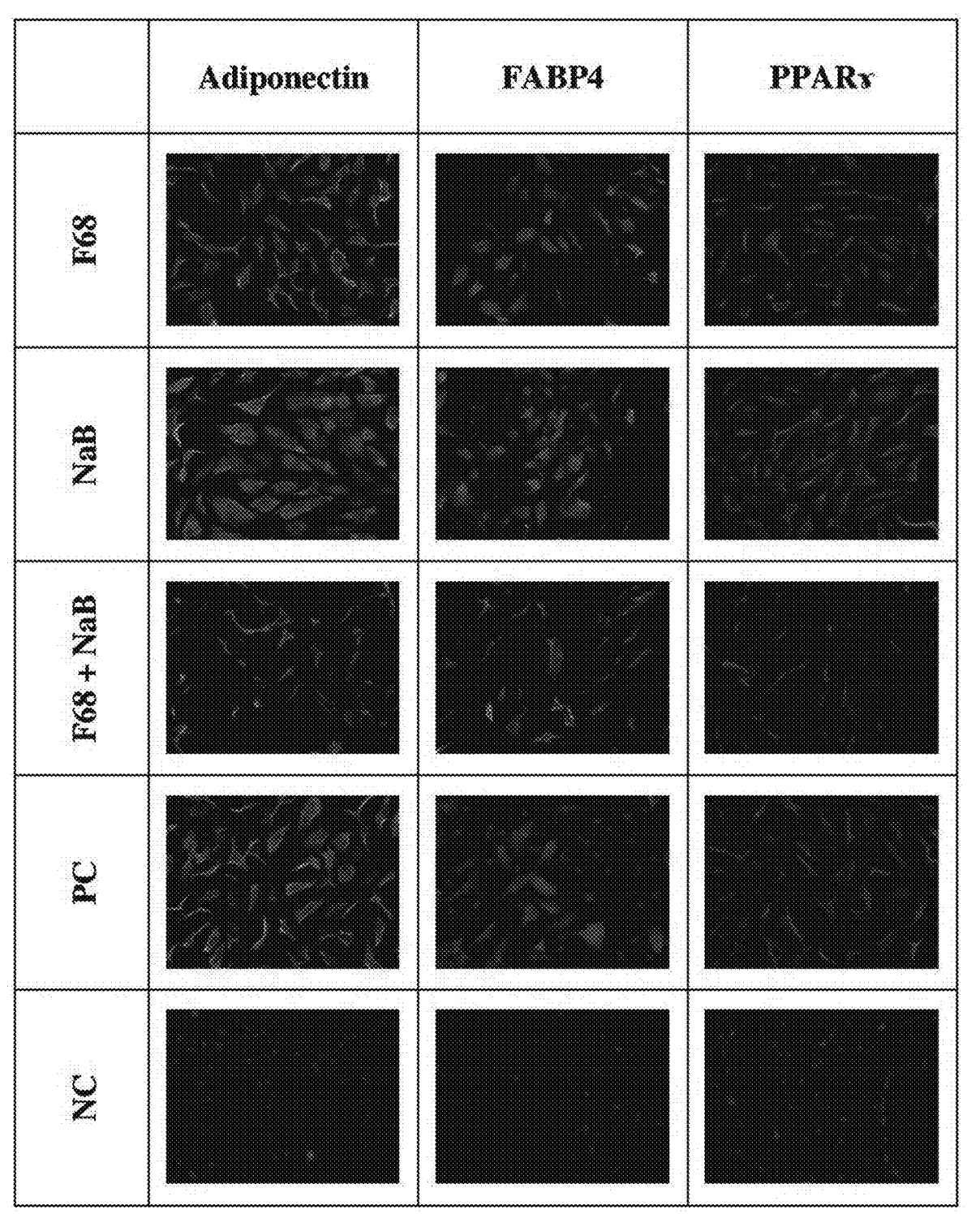
Figure 6:
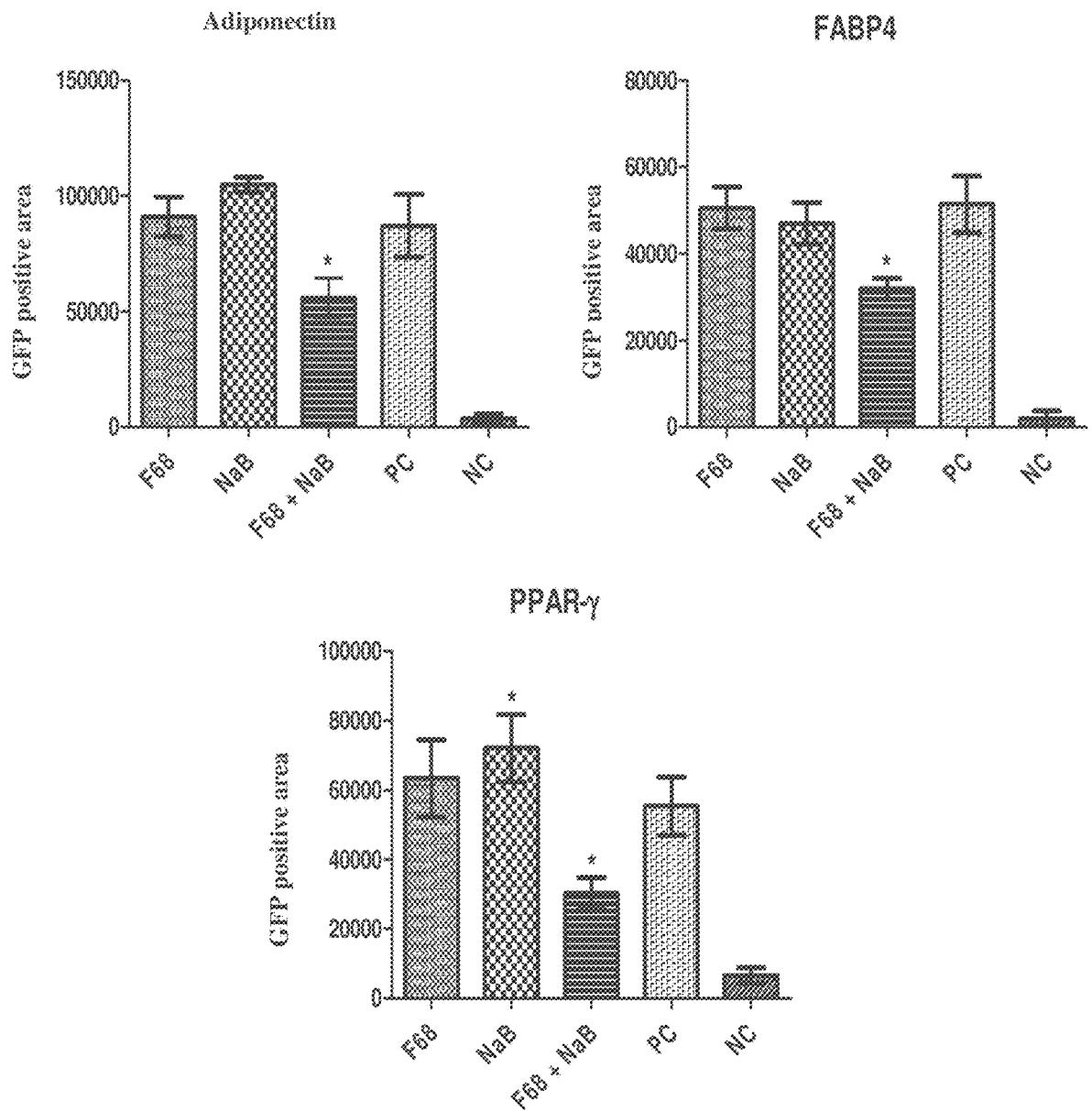
FIG. 6 shows the results of the graphical analysis of the immunocytochemistry results for Adiponectin, FABP4 and PPAR-γ proteins performed using Adobe Creative Suite 6 Program. PC: Positive control, NC: Negative control.

PPARγ, FABP4 and adiponectin protein expression levels were examined by immunocytochemistry method (FIG. 5). The amount of the proteins marked by the help of the secondary antibodies in green fluorescent was analyzed by the Adobe Creative Suite 6 program (FIG. 6). As a result of this experiment, the levels of protein expression levels when F68 and NaB were administered alone were higher than that of positive control, whereas the administration of the F68-NaB combination at the same ratios showed a significant decrease in protein expression levels (FIG. 5 and FIG. 6).

Figure 7:
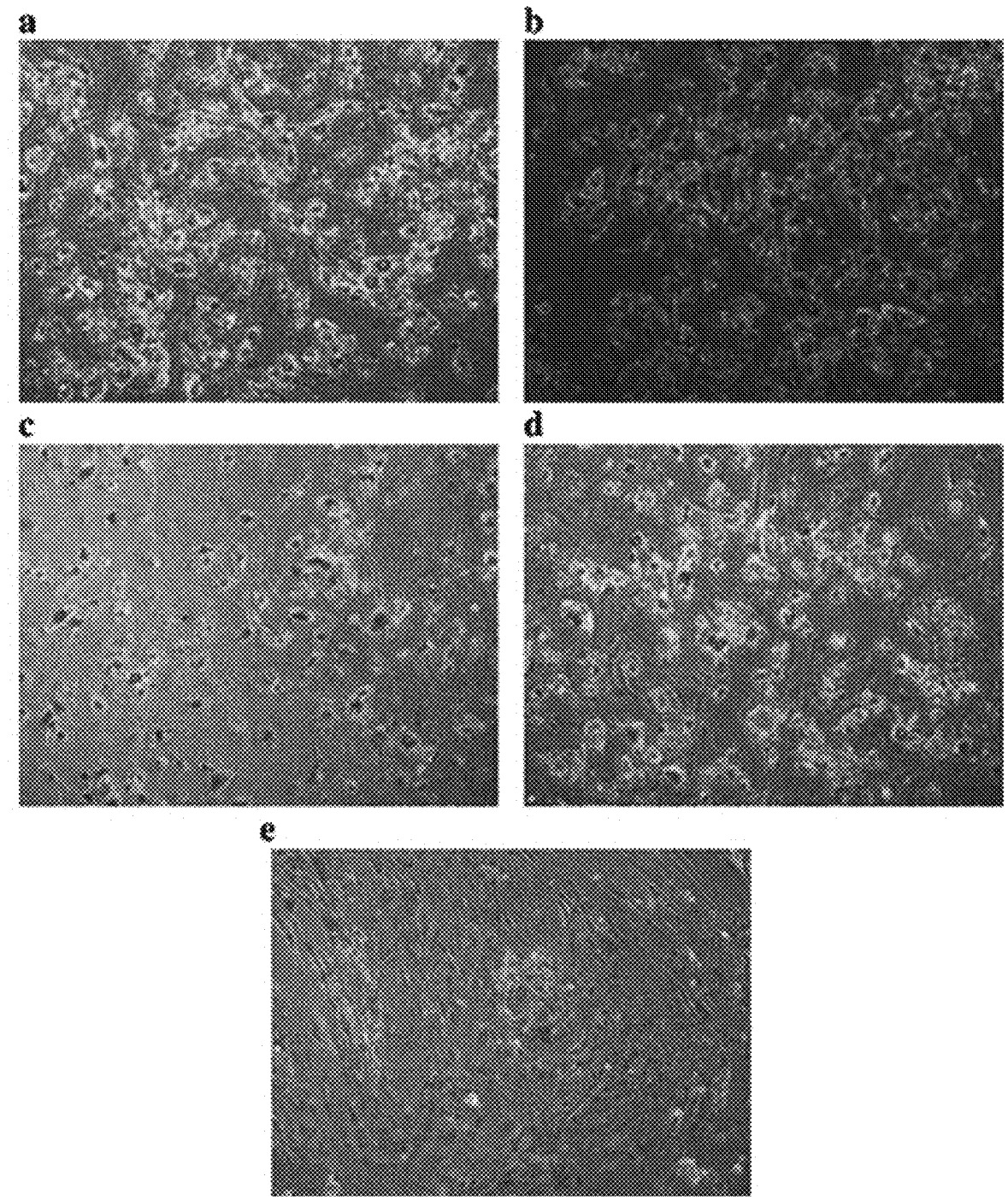
FIG. 7 shows 'Oil Red O' staining. a. F68, b. NaB, c. F68+NaB, d. positive control, e. negative control.
Figure 8:
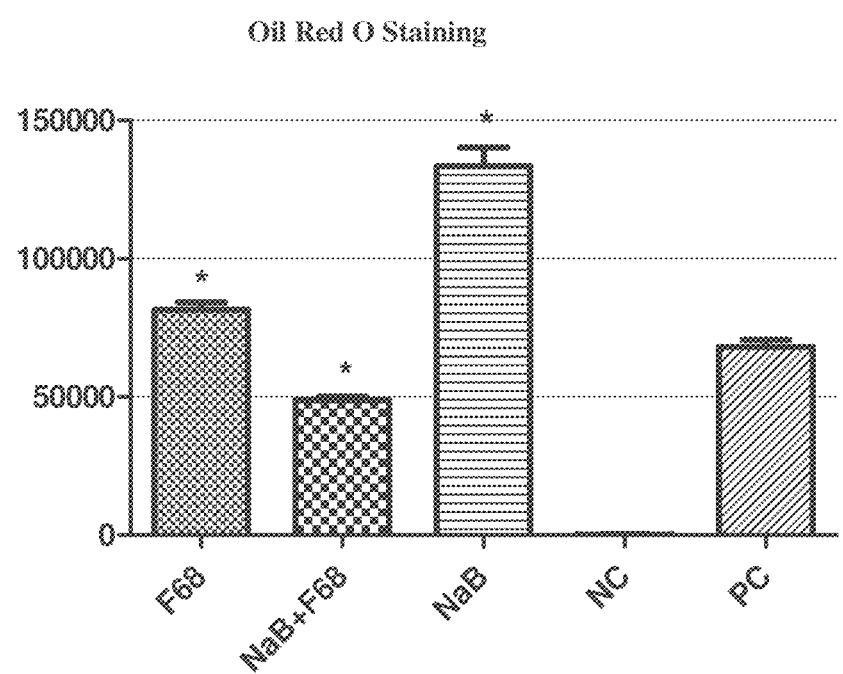
FIG. 8 shows the analysis of 'Oil Red O' staining using Adobe Creative Suite 6 Program. PC: Positive control, NC: Negative control. *$p<0.05$ compared to positive control.

'Oil Red O' staining is used to determine the amount of fat retained by adipogenic cells. In this study, it was shown that while the F68 and NaB administered alone at the doses determined in this study increased the amount of fat accumulation in the cells, the combination of NaB and F68 inhibited the adipogenic transcriptional program that causes fat accumulation in the cells (FIGS. 7 and 8). The NaB dosage used was chosen to be particularly low and at a non-cytotoxic level (FIG. 3). Despite that, the effect seen at high doses of NaB could be achieved when administered in combination with F68. In this context, a safe and effective complex, which has not yet been shown in the literature, has been developed to prevent adipogenesis that is the basis of obesity.

The following basic boron compounds can be used for application of the invention: boric acid, alkaline or alkaline earth metal borates (lithium borates such as lithium tetraborate, lithium metaborate, lithium pentaborate; sodium borates such as sodium metaborate, sodium hexaborate, sodium tetraborate, sodium octaborate; potassium borates such as potassium tetraborate, potassium metaborate, potassium hexaborate, potassium octaborate; calcium borates such as calcium diborate, calcium metaborate, calcium tetraborate, tricalcium tetraborate, pentacalcium tetraborate, calcium hexaborate; magnesium borates such as magnesium metaborate, magnesium diborate, trimagnesium tetraborate, pentamagnesium tetraborate) or all hydrate forms thereof, ammonium borates (ammonium metaborate, ammonium tetraborate, ammonium pentaborate and ammonium octaborate), boric acid esters (monomethyl borate, dmethyl borate, trimethyl borate, monoethyl borate, diethyl borate, triethyl borate, monopropyl borate, dipropyl borate, tripropyl borate, monobutyl borate, dibutyl borate or tributyl borate).

In application of the invention, particularly F68 but also F127, P106, P407, P85, P123 can be used as the Pluronic®.

Pluronic® P123 is the tradename for a triblock copolymer manufactured and/or sold by the BASF Corporation among others. The nominal chemical formula is $HO(CH_2CH_2O)_{20}(CH_2CH(CH_3)O)_{70}(CH_2CH_2O)_{20}H$, which corresponds to a molecular weight of around 5800 g/mol. Triblock copolymers based on poly(ethylene glycol)-poly(propylene glycol)-poly(ethylene glycol) are known generically as poloxamer, and similar materials are manufactured by other companies. Poloxamers have behaviors similar to those of hydrocarbon surfactants, and will form micelles when placed in a selective solvent such as water.

What is claimed is:

1. A method for treating obesity comprising administering to a person in need of treatment thereof a composition for obesity treatment, the composition comprising: a combination of a triblock copolymer with a nominal chemical formula of $HO(CH_2CH_2O)_{20}(CH_2CH(CH_3)O)_{70}(CH_2CH_2O)_{20}H$ and molecular weight of 5800 g/mol, and a boron compound selected from the group consisting of lithium borates, potassium borates, calcium borates, magnesium borates, and ammonium borates, wherein the boron compound suppresses expression levels of adipogenesis-promoting genes, and wherein the triblock copolymer solution is 1%, 0.7%, 0.5%, 0.3%, 0.1%, 0.05%, or 0.01% by weight/volume and the boron compound is at a dose of 5, 10, 20, 50, 100, 200 or 300 µg/ml.

2. The method for treating obesity according to claim 1, wherein the triblock copolymer reduces cytotoxic effects of the boron compound on adipose cells, wherein the triblock copolymer increases cell viability of adipose cells by at least 101%.

3. A method of using a composition effective on human adipose stem cells (HASC) for obesity treatment, the composition comprising a combination of a triblock copolymer with a nominal chemical formula of $HO(CH_2CH_2O)_{20}(CH_2CH(CH_3)O)_{70}(CH_2CH_2O)_{20}H$ and molecular weight of 5800 g/mol, and a boron compound selected from the group consisting of lithium borates, potassium borates, calcium borates, magnesium borates, and ammonium borates, the method comprising: dissolving the boron compound at a dose of 5, 10, 20, 50, 100, 200, or 300 µg/ml and the triblock copolymer at a concentration of 1%, 0.7%, 0.5%, 0.3%, 0.1%, 0.05%, or 0.01% by weight/volume to form the composition and then applying the composition to the adipose cells.

4. The method of using a composition effective on human adipose stem cells (HASC) for obesity treatment according to claim 3, wherein the triblock copolymer reduces cytotoxic effects of the boron compound on the adipose cells, wherein the triblock copolymer increases cell viability of adipose cells by at least 101%.

* * * * *